United States Patent [19]
Forkey et al.

[11] Patent Number: 5,980,453
[45] Date of Patent: Nov. 9, 1999

[54] ENDOSCOPE WITH LOW DISTORTION

[75] Inventors: Richard E. Forkey, Westminster; Brian E. Volk, Holden, both of Mass.

[73] Assignee: Precision Optics Corporation, Gardner, Mass.

[21] Appl. No.: 08/883,216

[22] Filed: Jun. 26, 1997

Related U.S. Application Data

[63] Continuation-in-part of application No. 08/605,593, Feb. 22, 1996, abandoned.

[51] Int. Cl.⁶ .................................................. A61B 1/002
[52] U.S. Cl. ............................ 600/162; 600/176; 600/171
[58] Field of Search .................................. 660/176, 171, 660/160, 103, 164, 162; 359/664, 663, 656

[56] References Cited

U.S. PATENT DOCUMENTS

| | | |
|---|---|---|
| 2,927,574 | 3/1960 | Scholz . |
| 4,267,828 | 5/1981 | Matsuo ..................................... 600/164 |
| 4,319,563 | 3/1982 | Kubota ..................................... 600/164 |
| 4,805,598 | 2/1989 | Ueda . |
| 4,934,771 | 6/1990 | Rogers . |
| 4,989,034 | 1/1991 | Hougaard . |
| 5,138,487 | 8/1992 | Ahn . |
| 5,150,249 | 9/1992 | Montagu . |
| 5,175,650 | 12/1992 | Takayama et al. . |
| 5,233,473 | 8/1993 | Kanamori . |
| 5,327,283 | 7/1994 | Zobel . |
| 5,416,638 | 5/1995 | Broome . |
| 5,424,877 | 6/1995 | Tsuyuki et al. . |
| 5,547,457 | 8/1996 | Tsuyuki et al. . |

FOREIGN PATENT DOCUMENTS 1157932   7/1969   United Kingdom .

*Primary Examiner*—John P. Leubecker
*Attorney, Agent, or Firm*—Pearson & Pearson

[57] ABSTRACT

An endoscope with an eyepiece and an objective lens system used for observing an object in an environmental media. The distal most optical element in the objective lens system is a spherical lens. The spherical lens has a curved distal surface that contacts the environmental media. The objective lens system facilitates the control of the distortion in an image generated by the objective lens system to approximate a reverse distortion of the eyepiece system measured as the distortion in an image generated distally of the eyepiece system of an object positioned proximally of the eyepiece system.

11 Claims, 7 Drawing Sheets

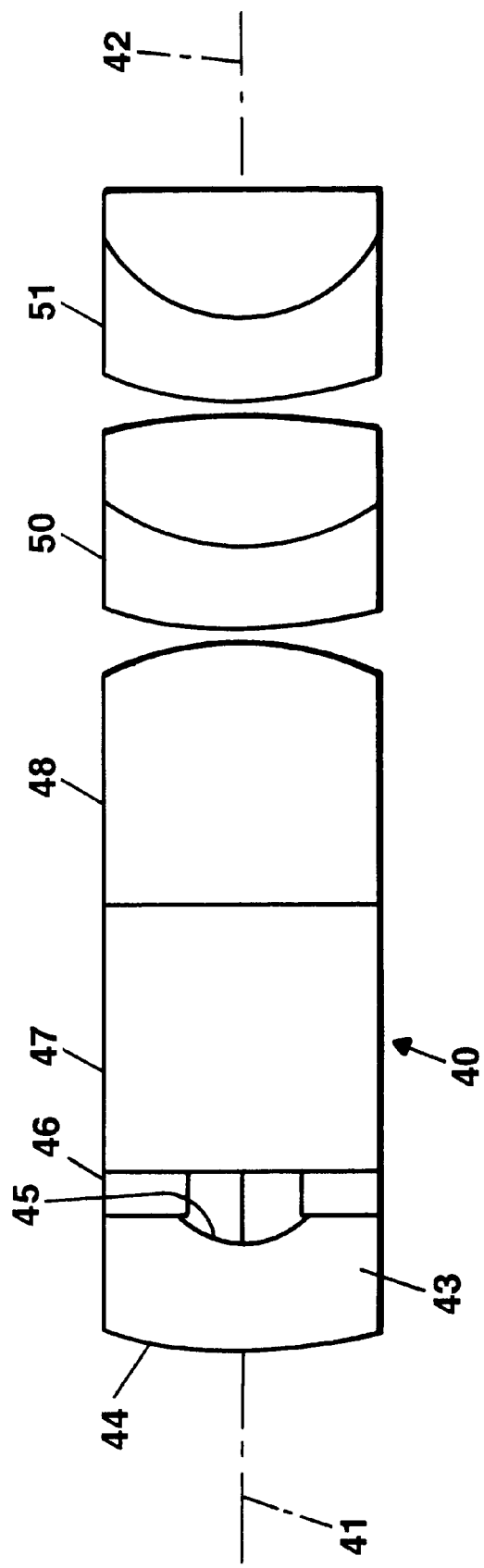

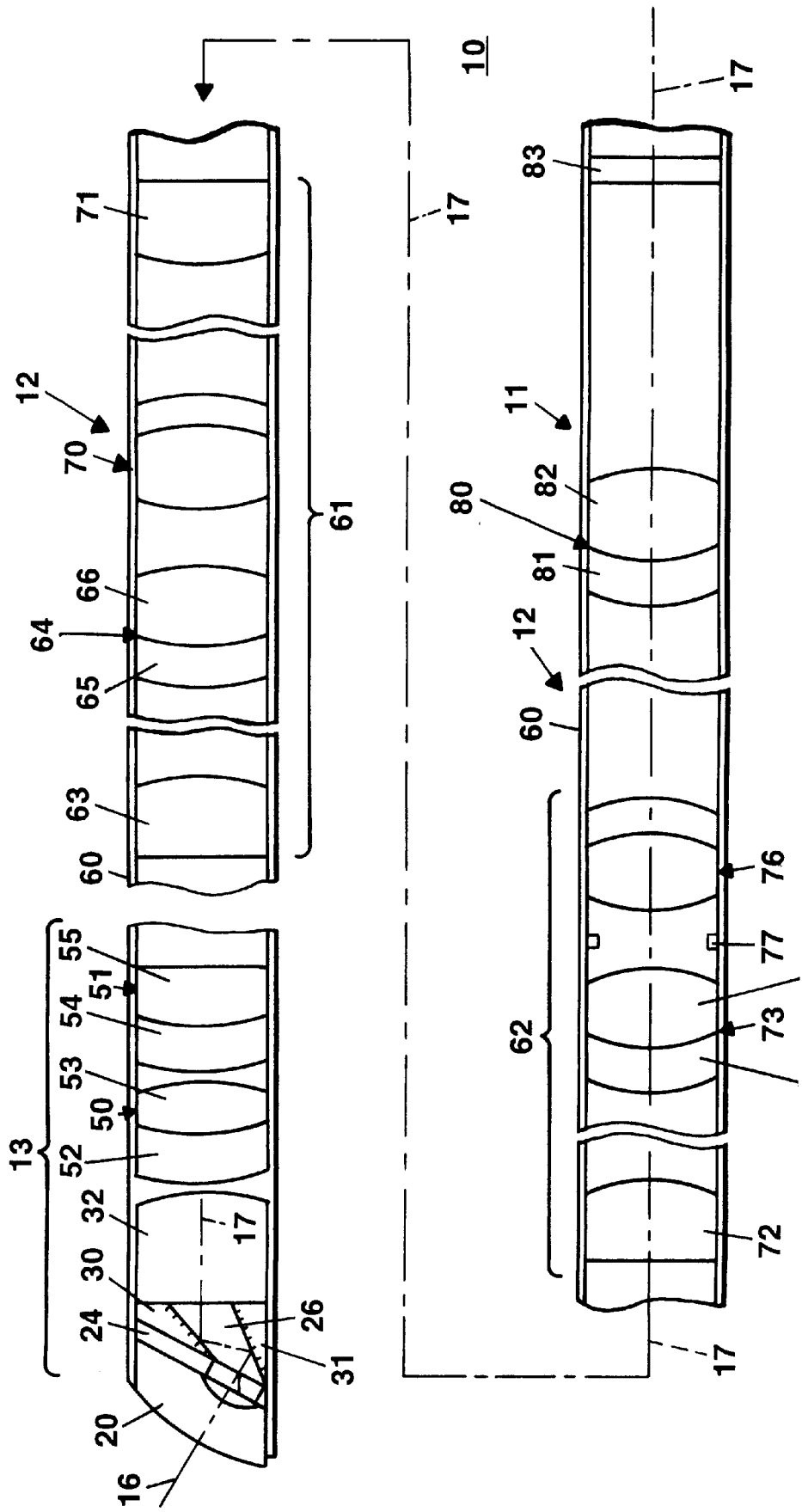

FIG. 6A

| REF. NO. | RADIUS OF CURVATURE | | THICKNESS | APERTURE DIAMETER | | MEDIUM |
|---|---|---|---|---|---|---|
| | FRONT | BACK | | FRONT | BACK | |
| 20 | 5.2030 CX | 0.9500 CC | 1.0000<br>0.2714 | 2.2000 | 1.3296 | TAF4 Hoya |
| 24 | INF | INF | 0.4060 | 0.9357 | | AIR |
| 26 | | | 0.5450 | 0.7227 | | PRISM |
| 30 | | | -1.1450 | 1.5995 | | |
| 31 | | | 0.8300 | | | AIR |
| 32 | INF | -3.3000CX | 2.5000 | 2.0000 | 2.6140 | TAF4 Hoya |
| | | | 0.1000 | | | AIR |
| 52 | 6.0630 CX | 2.6780 CC | 0.8000 | 2.6140 | 2.6140 | FDS30 Hoya |
| 53 | 2.6780 CX | -7.9000 CX | 1.2500 | 2.6140 | 2.6140 | BACD11 Hoya |
| | | | .01000 | | | AIR |
| 54 | 4.1400 CX | 1.6700 CC | 0.0800 | 2.6140 | 2.3099 | FDS30 Hoya |
| 55 | 1.6700 CX | -25.0900 CX | 1.2500 | 2.3099 | 2.2547 | BACD11 Hoya |
| | | | 2.4420 | | | AIR |
| | | | | 2.6000 | | IMAGE |
| | | | 2.9983 | | | AIR |
| 63 | INF | -8.4200 CX | 2.000 | 2.6140 | 2.6140 | BACD2 Hoya |
| | | | 10.9540 | | | AIR |
| 65 | 10.1900CX | 4.0000CC | 1.0000 | 2.6140 | 2.6140 | F1 Hoya |
| 66 | 4.0000CX | -29.8000CX | 2.3000 | 2.6140 | 2.6140 | BAK2 Scho |
| | | | 0.5000 | | | AIR |
| 70 | 29.8000CX | -4.0000CX | 2.3000 | 2.6140 | 2.6140 | BAK2 Scho |
| | -4.0000CC | -10.1900CX | 1.0000 | 2.6140 | 2.6140 | F1 Hoya |
| | | | 10.9540 | | | AIR |
| 71 | 8.4200 CX | INF | 2.000 | 2.6140 | 2.6140 | BACD2 Hoya |
| | | | 5.9966 | | | AIR |

| REF. NO. | RADIUS OF CURVATURE | | THICKNESS | APERTURE DIAMETER | | MEDIUM |
|---|---|---|---|---|---|---|
| | FRONT | BACK | | FRONT | BACK | |
| | OTHER RELAY SETS | | | | | |
| | | | 5.9966 | | | AIR |
| 72 | INF | -8.4200 CX | 2.0000 | 2.6140 | 2.6140 | BACD2 Hoya |
| | | | 10.9540 | | | AIR |
| 74 | 10.1900CX | 4.0000CC | 1.0000 | 2.6140 | 2.6140 | F1 Hoya |
| 75 | 4.0000CX | -29.8000CX | 2.3000 | 2.6140 | 1.5880 | BAK2 Scho |
| 77 | | | | | 1.5880 | APERTURE STOP |
| | | | 0.4900 | | | AIR |
| 76 | 29.8000CX | -4.0000CX | 2.3000 | 1.5880 | 2.6140 | BAK2 Scho |
| | -4.000CC | -10.1900 | 1.0000 | 2.6140 | 2.6140 | F1 Hoya |
| | | | 16.8442 | | | AIR |
| | | | | | 2.5859 | IMAGE |
| | | | 14.1372 | | | AIR |
| 81 | 12.7400CX | 6.3400CC | 1.7500 | 5.6000 | 5.6000 | SF4 Schot |
| 82 | 6.3400CX | -11.5000CX | 3.5000 | 5.6000 | 5.6000 | K7 Shott |
| | | | 13.0000 | | | AIR |
| 83 | INF | INF | 1.0000 | 5.6000 | 5.6000 | BK7 Sch |
| | | | 13.4815 | | | AIR |
| | | | | | 1.4687 | IMAGE |
| | | | 34.8800 | | | AIR |
| | INF | | | | 5.6898 | IMAGE |

FIG. 6B

ENDOSCOPE WITH LOW DISTORTION

CROSS REFERENCE TO RELATED APPLICATION

This is a continuation-in-part of application Ser. No. 08/605,593 filed Feb. 22, 1996 assigned to the same assignee as this application and now abandoned.

BACKGROUND OF THE INVENTION

1. Field of the Invention

This invention generally relates to optical systems and more specifically to endoscopes and the design of objective and related optical systems used in such endoscopes.

2. Description of Related Art

Endoscopes have obtained great acceptance within the medical community in connection with a number of procedures primarily because they provide a means for performing procedures with minimal patient trauma by enabling a physician to view directly the internal anatomy of a patient. Over the years a number of endoscopes have been developed and have been categorized according to specific applications. Many have specific names including arthroscopes, cystoscopes, proctoscopes, laparoscopes.

Generally, in whatever form, an endoscope comprises an objective lens system at the distal end of the endoscope that forms an image of an object within a patient in some environmental media such as air, water, a saline solution or the like. An eyepiece or ocular system at the proximal end presents the image for viewing visually, electronically or otherwise externally of a patient. An image transfer system intermediate the objective and the eyepiece systems transfers the image produced by the objective lens system to the eyepiece system.

Significant efforts have been undertaken to improve the optical designs of these endoscopes with attention at various times directed to individual ones of the constituent optical systems. However, as known, a number of diverse optical elements introduce various aberrations, distortions and other optical problems that can affect the quality of the image which the physician views. Moreover, the presence of these problems and attempts to compensate for them or cancel them complicate the design process. The design process is further complicated because the number of variables available to an optical designer for designing each of the objective, image transfer and eyepiece systems individually and collectively is generally less than required to individually compensate each source of optical problem. Consequently a final design normally is what the optical designer considers a reasonable compromise for a particular application.

For example, U.S. Pat. No. 5,175,650 to Takayama et al. discloses an objective lens system designed for an endoscope having a short total length, a small outside diameter and a wide field angle. According to this design, the objective lens system includes a front negative lens unit, an aperture stop, a positive lens unit and an infrared cut filter. This system allows rays to be incident on the filter at heights lower than the outside circumference of the filter thereby to correct certain distortions inherent in such an endoscope.

U.S. Pat. No. 5,327,283 to Zobel discloses another optical system for an endoscope with an objective with an object-side negative lens cluster to reduce image scale defects, such as distortion and field curvature. In this objective the object-side negative lens cluster comprises two menisci each having a negative refractive power to reduce the defects of distortion and to produce a flattened image field.

As another example, U.S. Pat. No. 5,416,638 to Broome discloses an endoscope that includes a transfer module, or relay lens unit, an objective element and an eyepiece, or ocular element. The objective element includes a distal glass window having a plano-spherical shape or plano-aspherical shape, a prism and a plurality of lenses all of which produce an image for transfer through the transfer module to the eyepiece. This particular design is adapted to minimize adverse effects of certain sources of aberration by transferring residual aberration in the image formed by the objective element to the ocular element for correction.

As previously indicated, the distal end of an endoscope is introduced into and objects viewed through a wide variety of environmental media. Initially a physician may test the endoscope by viewing an object in air. In actual use the physician may view an object while the distal end of the endoscope is immersed in a fluid, such as water, saline solutions, air or carbon dioxide. Conventionally an optical designer may optimize the design for viewing in a fluid characterized by a particular index of refraction and thereby accept any distortion and other aberrations that might occur when imaging an object in a fluid having a different index of refraction. U.S. Pat. No. 5,424,877 to Tsuyuki et al. discloses such a design that is adapted for allowing the observation of objects located in liquids. Each disclosed embodiment includes a window with a distal most surface having either a planar or aspherical surface.

Taken collectively, the foregoing references disclose various objective lens system optical designs for meeting some particular design criterion. In each, however, the designs involve a window at the distal-most position that defines either a planar or aspherical distal most surface. Windows with aspherical surfaces generally have not been used in practical systems even though the use of one or more aspherical surfaces would introduce another set of multiple lens design variables. Those optical systems that incorporate aspherical surfaces apparently do so for reasons other than controlling distortion.

U.S. Pat. No. 4,805,598 to Ueda discloses an optical system with lenses and a highly-viscous gel-like substance that is free from any water vapor. Ueda's primary objective was to produce an endoscope that resists clouding. Ueda, in one embodiment, discloses a distal-most objective lens element with an exterior radiused convex surface with a concave central surface on the proximal side. A series of another proximally facing spherical lens, biconcave lens and biconvex lens produce an image. In another embodiment, Ueda discloses the double spherical lens located behind a distal window. A fiberoptic or relay lens image transfer section produces an image at an eyepiece or CCD device.

U.S. Pat. No. 5,547,457 to Tsuyuki et al. discloses eight embodiments of objective lens systems adapted to be interchangeable on the distal end of an endoscope as the need arises to view objects. A distal most lens has a convex distal surface and is a negative lens. The second lens is a positive lens to form a real image. It is stated that the introduction of the negative lens allows the final image to be flatter and allows greater correction of aberrations at long and short distances. A second of these embodiments incorporates a distal most spherical lens surface. Other embodiments include planar distal most lens surfaces. Tsuyuki et al. also disclose that the distortion at the full field of view can approach 50%.

Great Britain Patent No. 1,157,932 discloses an endoscope in which two lenses form an inverted teleplate objective lens.

None of the Ueda, Tsuyuki et al. or Great Britain patents describes or suggests any control over the distortion that the lens systems introduce into the final image. Each seems to have designed an optical system with paramount interest in the control of other parameters, all to the detriment of distortion, particularly in the case of the lens systems that the Tsuyuki et al. patent discloses.

Indeed, commercially available endoscopes historically have been manufactured and continue to be manufactured with windows that have a planar surface exposed to the environment and the designers of endoscopes continue to develop lens systems without the additional degree of freedom that a non-planar surface would introduce even summarily accepting changes in distortion and other aberrations that can result when an object is viewed through different environmental media.

SUMMARY

Therefore, it is an object of this invention to provide an endoscope that incorporates an objective lens system that provides greater flexibility in the design of an endoscope.

Another object of this invention is to provide an endoscope that incorporates an objective lens system that minimizes changes in the distortion of an image at an eyepiece as an image is viewed through different environmental media.

In accordance with this invention, an objective lens system at the distal end of an endoscope includes a spherical objective lens system, an eyepiece system and an image transfer system. The objective lens system forms an image for transfer through said endoscope to the eyepiece system. The objective lens system presents a curved distal surface to the environment and introduces a distortion into the image generated by the objective lens system. The spherical surface facilitates control of the distortion to a value that approximates the distortion the eyepiece introduces into an image generated distally thereof of an object proximal to the eyepiece system.

BRIEF DESCRIPTION OF THE DRAWINGS

The appended claims are intended to point out with particularly and to claim distinctly the subject matter of this invention. The various objects, advantages and novel features of this invention will be more fully apparent from a reading of the following detailed description in conjunction with the accompanying drawings in which like reference numerals refer to like parts, and in which:

FIG. 4 is a cross-sectional view of another embodiment of this invention;

FIG. 5 is a cross-sectional view of a specific embodiment of an endoscope constructed in accordance with this invention; and FIGS. 6A and 6B constitute a table that identifies one specific embodiment of the endoscope shown in FIG. 5.

DESCRIPTION OF ILLUSTRATIVE EMBODIMENTS

Figure 1:
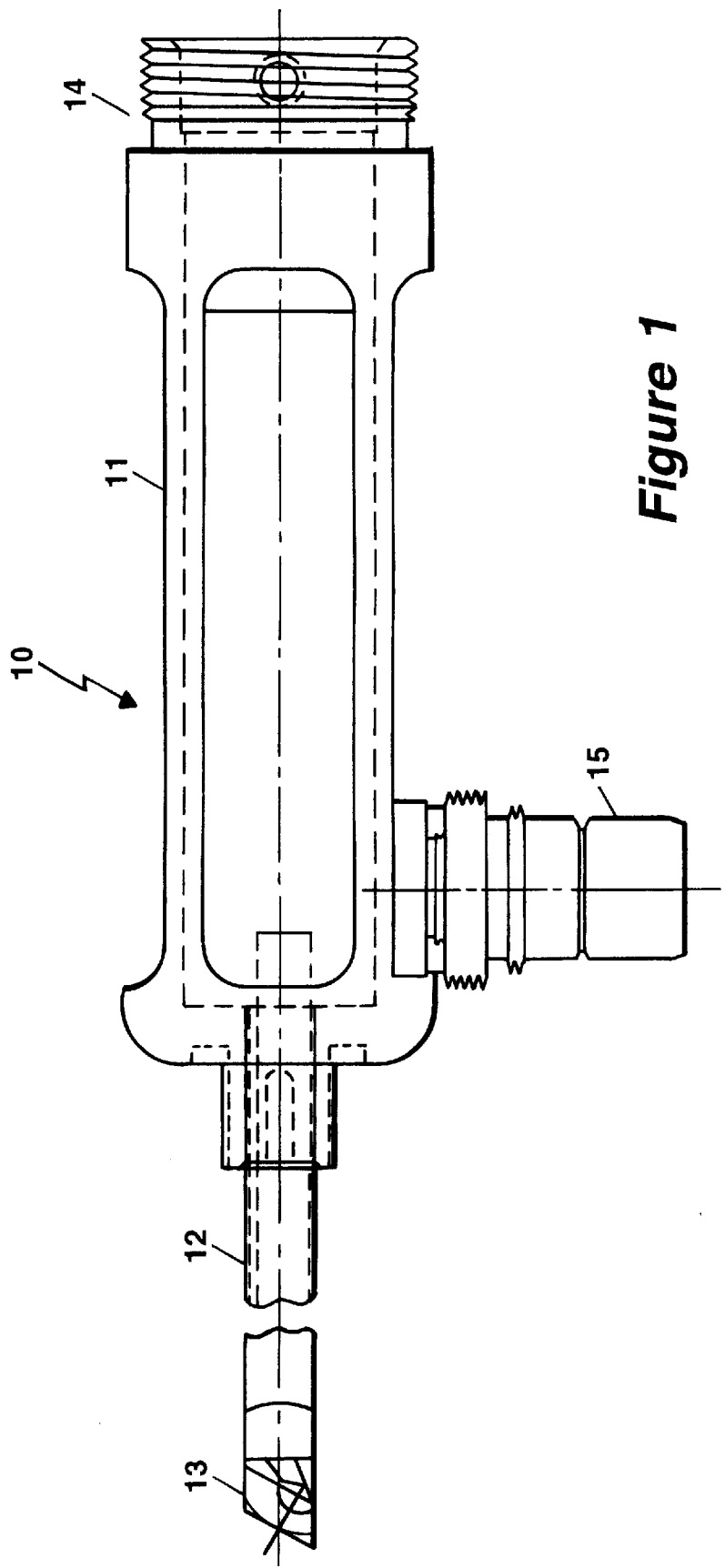
FIG. 1 is a diagram of an endoscope that can incorporate this invention.

FIG. 1 depicts an endoscope 10 that includes an eyepiece system 11 at the proximal end of an image transfer system 12 and an objective lens system 13 at the distal end of the image transfer system 12. The eyepiece system 11 includes an adapter 14 for connection to a viewing device, such as a video camera, and another adapter 15 for connection to a light source. The image transfer system 12 includes a plurality of relay lenses or the like for transferring the image formed by the objective lens system 13 to the eyepiece system 11. As the optical components of the image transfer system 12 and the methods for designing such systems are well known in the art, they are not shown in detail. Moreover, as also known in the art, a conventional image transfer system can be designed to introduce essentially no distortion into the image.

Figure 2:
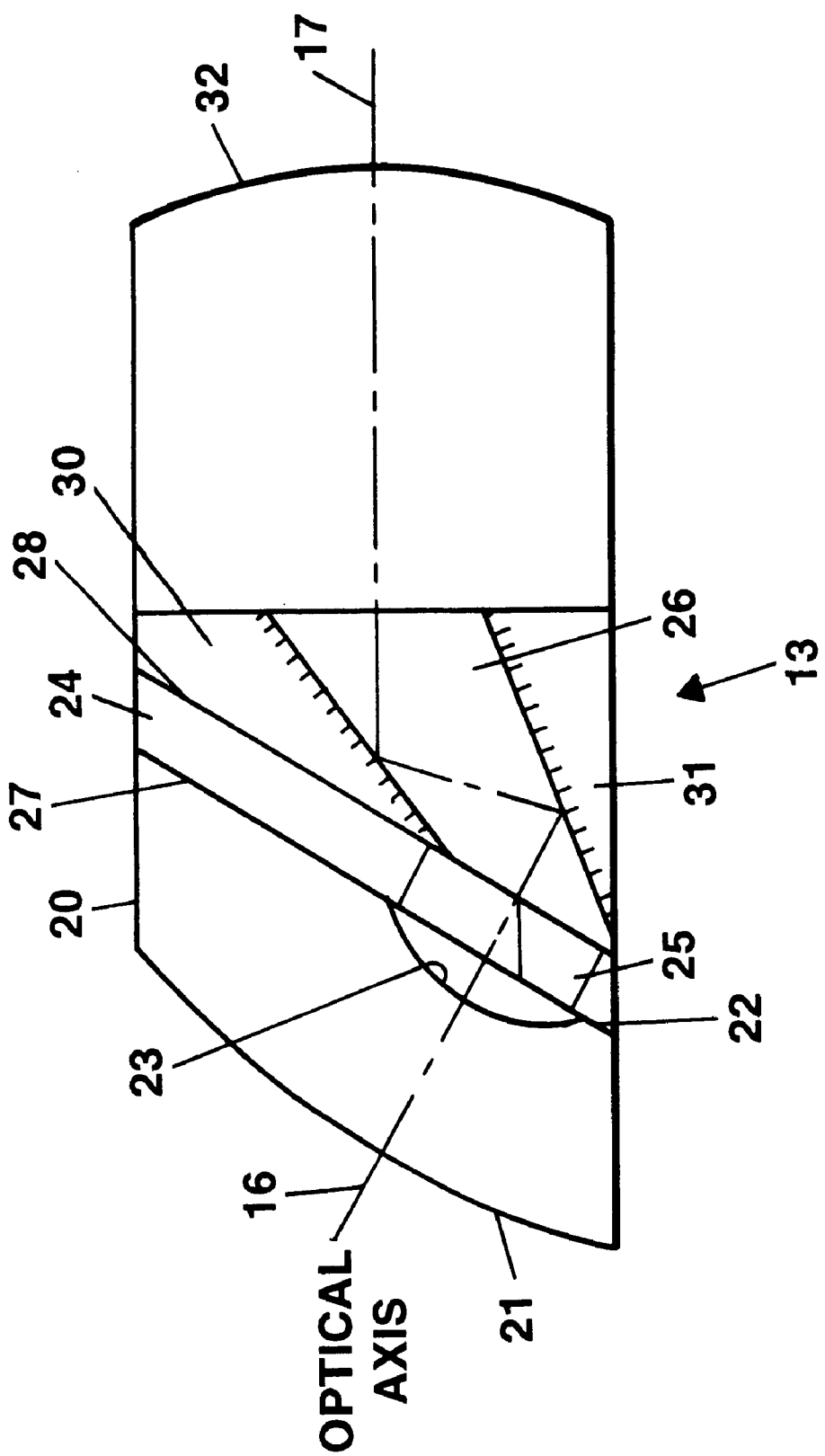
FIG. 2 is a cross sectional view of an objective lens system for used in the endoscope of FIG. 1 that incorporates this invention.
Figure 3:
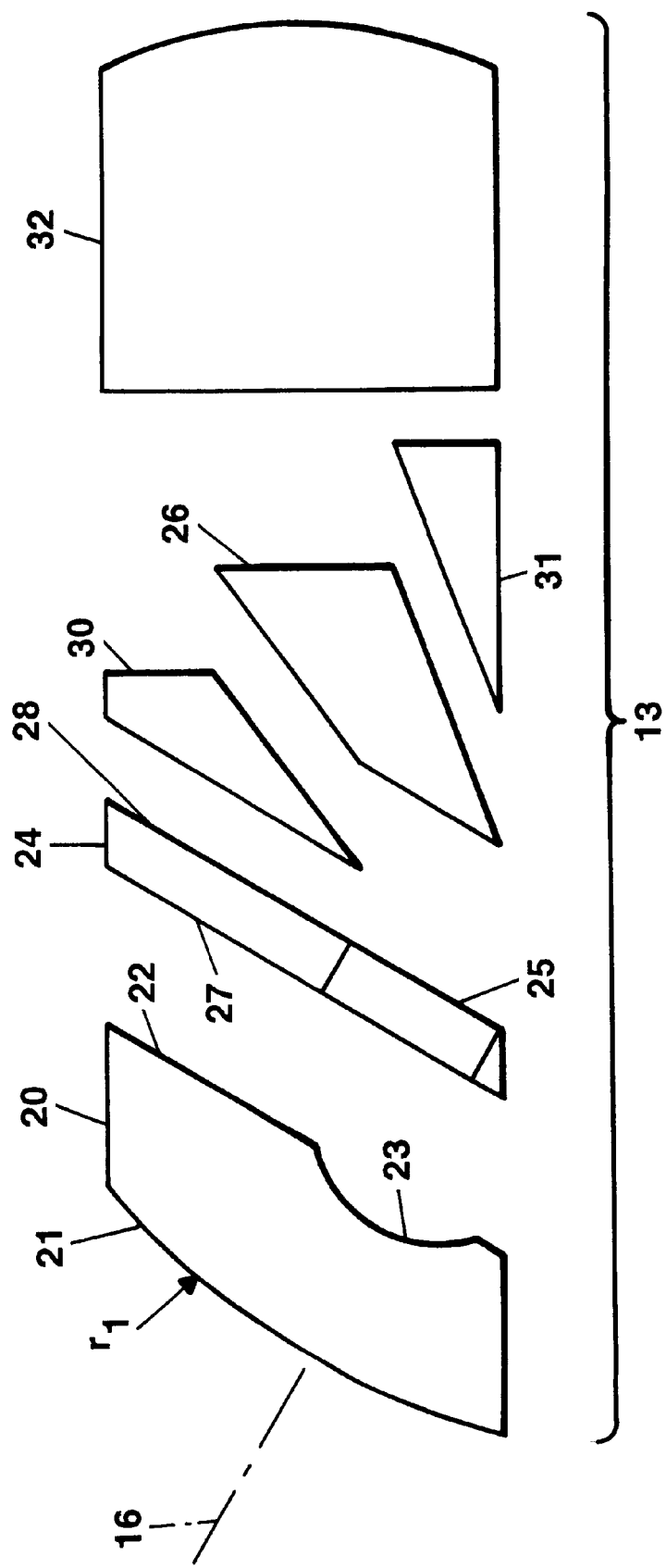
FIG. 3 is an exploded view of the objective lens system shown in FIG. 2.

FIGS. 2 and 3 depict one embodiment of the objective lens system 13 in detail without any support structures, such as internal and external coaxial sheaths that support and position individual elements within the objective lens system with respect to each other and with respect to the image transfer system 12. In the embodiment shown in FIGS. 1 through 3, the objective lens system 13 produces an image of an object in a field of view centered on a first optical axis 16 and routes the image to a second optical axis 17 that extends from the objective lens system 13 and that constitutes the central axis of the endoscope 10, particularly the image transfer system 12.

In accordance with this invention, the most distal element in the objective lens system 13 is a spherical lens 20. This spherical lens 20 has a distal surface 21 and a proximal surface 22. The distal surface 21, by virtue of being the most distal surface, directly contacts the environmental media surrounding the object being imaged, so the surface 21 constitutes a refracting surface because the indices of refraction for the environmental media and the glass forming the spherical lens 20 will be different. For example, if the object is viewed in water and the spherical lens 20 is formed of optical glass, the indices of refraction are typically 1.3 and 1.79, respectively.

To achieve the objects of this invention, the surface 21 is curved, not planar. That is, the radius of curvature for the surface 21, $r_1$, is less than infinity; $r_1 < \infty$. Providing this spherical surface enables an optical designer to control the radius, $r_1$, and thereby obtain another degree of control over the characteristics of the objective lens system 13 and the endoscope 10, particularly the distortion that the objective lens system 13 introduces. As will become apparent controlling this distortion in conjunction with a distortion of the eyepiece system 11 by controlling this radius can minimize distortion that occurs in conventional endoscopes of similar design when a planar surface is substituted for the curved surface 21. In addition, it has been observed that reasonable changes in the index of refraction of the environmental media have minimal adverse effects on distortion. In some cases, the image delivered from the eyepiece system 11 in FIG. 1 can even improve. As a result, physicians will observe essentially the same image of an object notwithstanding the nature of the environmental media or the distortion introduced by the objective lens 13 or eyepiece 11 individually.

In FIGS. 2 and 3, the proximal surface 22 of the spherical lens 20 is transverse to the optical axis 16. It includes a concave spherical surface 23 that broadens the field of view.

The remaining elements shown in FIGS. 2 and 3 complete the objective lens system 13. They function to fold the image received from the first optical axis 16 onto the second optical axis 17 and to form a real image of an object positioned along the optical axis 16.

An opaque shim 24 with an off-center aperture 25 spaces the spherical lens 20 with respect to a prism 26. The shim also limits extraneous light from entering the system beyond the shim 24. Abutting surfaces 27 and 28 also lie in planes that are transverse to the first optical axis 16 in the orientation shown in FIGS. 2 and 3. In addition, the thickness of the shim 24 and the depth of the spherical surface 23 determine an air space following the first element. The extent. of that air space along the first optical axis 16 controls the contribution of aberrations, as well known in the art.

The surface 28 also acts as a reference for positioning a pair of spaced supports 30 and 31 that position the prism 26 that folds the first optical axis 16 onto the second optical axis 17. The construction of such prisms is well known in the art.

As the image leaves the prism 26, it passes through a plano-convex lens 32 and is brought to focus as a real image. The imaged light then travels through the image transfer system 12 to the eyepiece system 11 for viewing.

It will now be apparent that in some applications, such as in arthroscopes, the diameter of the objective lens system 13 is so small (i.e., in the order of 3 mm. or less) that the surface 21 in FIGS. 2 and 3 can have a very small radius of curvature without producing any appreciable protrusion of the vertex of the lens 20 beyond the end of any protective sheath.

FIG. 4 depicts an objective lens system 40 that is analogous to the objective lens system 13 shown in FIGS. 2 and 3, but is adapted to have a common optical axis 41 that is coaxial with the optical axis 42 through the image transfer system 12. This objective lens system 40 includes a distal spherical lens 43 that has a curved spherical distal surface 44 and a curved spherical proximal surface 45. While the spherical lens 20 is oblique to the second optical axis 17 in FIGS. 1 through 3, the spherical lens 43 is transverse to the axis 42. An opaque shim 46 performs the same function as the shim 27. In this embodiment it is not necessary to fold the optical axis, so the shim 46 is intermediate the spherical lens 43 and a block 47 of optical glass that conveys light to a plano-convex lens 48. For the 0-degree application of FIG. 4, the block 47 is substituted for the prism 26 in FIGS. 1 through 3; the lenses 32 and 48 perform identical functions.

FIG. 4 additionally discloses two doublets 50 and 51 that can be used to reposition the image with respect to the following image transfer system 12. Such doublets can be considered as part of the objective lens system 13 or the image transfer system 12. If one considers them as part of the objective lens system 13, corresponding doublets would be added to the elements shown in FIGS. 2 and 3.

Thus, the endoscope 10 shown in FIGS. 1 through 4 and constructed in accordance with this invention enables the optical designer to achieve better control over distortion. For example, as previously described, similar endoscope constructions with a planar distal surface and a first optical axis 16 that is oblique to the second optical axis 17 produce an image with pronounced barrel distortion. The substitution of the spherical lens 20 with its curved distal surface 21 and control of distortion characteristics enable the production of an endoscope that essentially eliminates any noticeable barrel distortion. As also previously indicated, the curved distal surface 21 minimizes the introduction of any distortion produced when the environmental media for an object changes.

FIG. 5 depicts portions of one specific embodiment of the endoscope 10 that provides a low distortion image. That is the endoscope 10 produces an image with visually undetectable barrel distortion or pin cushion distortion. This embodiment utilizes the objective lens system 13 of FIG. 5 coupled with the doublets 50 and 51, a relay lens set 61 that forms a portion of the image transfer system 12, another lens set that forms a proximal lens set 62 and the eyepiece system 11. Reference numerals identifying the objective lens system 13 in FIGS. 1 and 4 identify corresponding elements in FIG. 5.

More specifically, the objective lens system 13 includes, from the distal end, the spherical objective lens 20, the shim 24, the prism including the elements 26, 30 and 31, the plano convex lens 32 and the doublets 50 and 51. In this particular embodiment the doublet lens 50 comprises a concave-convex lens 52 and a biconvex lens 53. The doublet 51 includes a concave-convex lens 54 and a plano-concave lens 55. All of these elements are disclosed as lying in a sheath 60 that extends proximally to retain the image transfer system 12 and the eyepiece system 11.

The lens set 61 represents one of multiple sets of relay lens sets. Each relay lens set has the same form. The relay lens set 61 includes, from the distal to proximal ends, a plano convex lens 63, a doublet 64 including a concave convex lens 65 and a biconvex lens 66. A doublet 70 has the same construction as the doublet 64 but is reversed 180°. A plano-convex lens 71 is the last lens in the lens set 61.

A final lens set 62 in the system is adjacent the eyepiece and comprises a plano-convex lens 72, a doublet 73 including lenses 74 and 75 and a doublet 76 having a corresponding construction but being disposed oppositely. However, this particular section eliminates the final plano-concave lens, such as the lens 71, to produce an image.

FIG. 5 depicts an aperture stop 77. The function of such an aperture stop is well known.

In the eyepiece system 11 a doublet 80 includes a concave-convex lens 81 and a biconvex lens 82 and a window 83. The doublet 80 forms an image that can be visualized by an individual looking in the eyepiece system 11.

The specific construction of an endoscope 10, such as shown in FIG. 5 can have many forms. FIGS. 6A and 6B list the various parameters of an embodiment of FIG. 5 that produces low distortion.

In accordance with this invention, the eyepiece system 11, comprising the doublet 80 and window 83, are optimized for various parameters of the endoscope. Then the distortion of the eyepiece is determined assuming that the eyepiece system 11 is imaging an object located proximally of the window 83. That is, the resulting distortion in the image to the distal side of the doublet 80 is determined. With this "reverse distortion" information, the objective lens system 13 can be calculated.

The addition of the distal spherical surface on the circle objective lens 20 facilitates the design of an objective lens system 13 to meet various optical criteria and, in combination therewith, control the distortion of the image generated proximally of the doublet 51. That is, changing the radius of the spherical lens 50 can have a dominant effect on distortion with less effect on other optical parameters such as field curvature and aberrations. It is the object of this procedure to provide an objective lens system 13 that has the required optical characteristics including a distortion that matches the reverse distortion of the eyepiece system 11. For an image transferred from the distal end through the proximal end, the result is that the distortions, if of the same type and magnitude, tend to offset. That is, if both lens systems produce proximally equal barrel distortions, the image from the endoscope will have a near-zero distortion. In fact it has been found that these procedures and this construction can produce an endoscope such as shown in FIG. 5 that has a distortion of less than 5%. It is difficult for an individual to perceive the distortion at this level.

In summary, there have been disclosed different embodiments of an endoscope that are particularly well adapted for use with small diameter endoscopes, such as arthroscopes, that are used to view objects located in diverse environmental media. The specific construction of the eyepiece and the objective lens systems with the distal most element comprising a spherical lens with a curved distal surface lies at the heart of this invention. More specifically, allowing the curved surface provides another design variable by which distortion can be eliminated or reduced to acceptable levels. Moreover, the curved surface seems also to limit the distortion that will be apparent as one such arthroscope is moved from one environmental medium to another.

This invention has been disclosed in terms of certain embodiments. It will be apparent that many modifications can be made to the disclosed apparatus without departing from the invention. For example, differently sized optical elements of different materials can be substituted for the specifically disclosed lenses and other optical elements. Therefore, it is the intent of the appended claims to cover all such variations and modifications as come within the true spirit and scope of this invention.

What is claimed as new and desired to be secured by Letters Patent of the United States is:

1. A low-distortion endoscope comprising:
    A. a sheath extending between proximal and distal ends,
    B. image transfer means in said sheath intermediate said proximal and distal ends for optically transferring an image from the distal end to the proximal end,
    C. eyepiece means at said proximal end of said sheath including a doublet lens for presenting the image for visualization proximally thereto, said eyepiece means being characterized by an eyepiece distortion characteristic representing the distortion that would be introduced into an image formed distally of said eyepiece means of an object positioned proximally of said eyepiece means, and
    D. objective lens means including a plurality of optical components at said distal end having, as the most distal of said optical components, a spherical objective lens for forming an image of an object positioned distally of said spherical objective lens for transfer through said image transfer means and said eyepiece means, said spherical objective lens facilitating the control of the distortion characteristic of said objective lens means to introduce distortion into the image from said objective lens means that approximates the eyepiece distortion characteristic.

2. An endoscope as recited in claim 1 wherein said endoscope is characterized by an optical axis at the distal end thereof and said spherical objective lens includes a distal spherical surface that forms an interface with the environment.

3. An endoscope as recited in claim 2 wherein another of said optical components in said objective lens means includes prism means proximally of said spherical objective lens for redirecting the image along an image axis.

4. An endoscope as recited in claim 3 wherein said objective lens means additionally includes shim means for spacing said prism means and said spherical objective lens, said shim means including an aperture therethrough for alignment on an extension of the image axis from said spherical objective lens.

5. An endoscope as recited in claim 3 wherein said objective lens means additionally includes a second lens on the image axis for receiving said image from said prism means.

6. An endoscope as recited in claim 5 wherein said objective lens means additionally includes shim means for spacing said prism means and said spherical objective lens, said shim means including an aperture therethrough for alignment on an extension of the image axis from said spherical objective lens and wherein said second lens abuts said prism at a proximal surface thereof.

7. An endoscope as recited in claim 6 wherein said objective lens system additionally includes first and second spaced doublets aligned proximally of said second lens.

8. An endoscope as recited in claim 7 wherein said eyepiece means includes a doublet lens spaced proximally of said image transfer means and a window spaced proximally of said doublet lens.

9. An endoscope as recited in claim 1 wherein said objective lens means include a plurality of lens elements intermediate said spherical objective lens and said image transfer means that define an optical axis that is coaxial with said image transfer means.

10. An endoscope as recited in claim 9 wherein said objective lens system additionally includes first and second spaced doublets aligned proximally of said plurality of lens elements.

11. An endoscope as recited in claim 10 wherein said eyepiece means includes a doublet lens spaced proximally of said image transfer means and a window spaced proximally of said doublet lens.

* * * * *